(12) United States Patent
Black et al.

(10) Patent No.: US 10,524,841 B2
(45) Date of Patent: *Jan. 7, 2020

(54) SPINE STABILIZATION SYSTEM

(71) Applicant: GLOBUS MEDICAL, INC., Audubon, PA (US)

(72) Inventors: Michael Black, Phoenixville, PA (US); Michal Zentko, Florham Park, NJ (US); Jason Pastor, Philadelphia, PA (US)

(73) Assignee: Globus Medical, Inc., Audubon, PA (US)

(*) Notice: Subject to any disclaimer, the term of this patent is extended or adjusted under 35 U.S.C. 154(b) by 188 days.

This patent is subject to a terminal disclaimer.

(21) Appl. No.: 15/849,730

(22) Filed: Dec. 21, 2017

(65) Prior Publication Data
US 2018/0110547 A1    Apr. 26, 2018

Related U.S. Application Data

(63) Continuation of application No. 12/874,845, filed on Sep. 2, 2010, now Pat. No. 9,877,747.

(60) Provisional application No. 61/239,309, filed on Sep. 2, 2009.

(51) Int. Cl.
*A61B 17/70* (2006.01)

(52) U.S. Cl.
CPC ...... *A61B 17/7044* (2013.01); *A61B 17/7055* (2013.01)

(58) Field of Classification Search
CPC combination set(s) only.
See application file for complete search history.

(56) References Cited

U.S. PATENT DOCUMENTS

| | | | |
|---|---|---|---|
| 4,946,458 A | 8/1990 | Harms | |
| 5,520,690 A | 5/1996 | Errico | |
| 5,549,608 A | 8/1996 | Errico | |
| 5,647,873 A | 7/1997 | Errico | |
| 5,667,508 A | 9/1997 | Errico | |
| 5,669,911 A | 9/1997 | Errico | |
| 5,672,176 A | 9/1997 | Biedermann | |
| 5,690,630 A | 11/1997 | Errico | |
| 5,713,898 A * | 2/1998 | Stucker | A61B 17/7044 606/280 |
| 5,733,285 A | 3/1998 | Errico | |
| 5,817,094 A | 10/1998 | Errico | |
| 5,899,904 A * | 5/1999 | Errico | A61B 17/7032 606/256 |

(Continued)

*Primary Examiner* — Lynnsy M Summitt

(57) ABSTRACT

Spine stabilization systems and methods for stabilizing the spine. In particular, the spinal stabilization system has an occipital plate configured with a central portion and at least two extension portions extending from the central portion. At least two rod receivers are positioned on each one of the at least two extension portions and the at least two rod receivers are adapted and configured to receive at least two elongated rods. At least two locking assemblies are adapted and configured to retain the at least two elongated rods within the at least two rod receivers. The occipital plate further includes a plurality of holes for receiving bone fasteners and includes a slot for receiving each one of the at least two rod receivers, and the rod receivers being capable of translating and rotating within the slots.

20 Claims, 9 Drawing Sheets

(56) References Cited

U.S. PATENT DOCUMENTS

| | | | |
|---|---|---|---|
| 5,928,233 A * | 7/1999 | Apfelbaum | A61B 17/7055 606/261 |
| 6,053,917 A | 4/2000 | Sherman | |
| 6,063,090 A | 5/2000 | Schlapfer | |
| 6,146,382 A | 11/2000 | Hurlbert | |
| 6,355,040 B1 | 3/2002 | Richelsoph | |
| 6,524,315 B1 * | 2/2003 | Selvitelli | A61B 17/7044 606/278 |
| 6,945,972 B2 * | 9/2005 | Frigg | A61B 17/7041 606/256 |
| RE39,089 E | 5/2006 | Ralph | |
| 7,303,563 B2 * | 12/2007 | Poyner | A61B 17/7044 606/250 |
| 7,572,282 B2 * | 8/2009 | Boomer | A61B 17/7055 606/280 |
| 7,585,312 B2 * | 9/2009 | Rawlins | A61B 17/7041 606/246 |
| 7,618,443 B2 * | 11/2009 | Abdou | A61B 17/6433 606/267 |
| 7,621,942 B2 * | 11/2009 | Piehl | A61B 17/8061 606/279 |
| 7,776,070 B2 * | 8/2010 | Null | A61B 17/7055 606/252 |
| 8,147,527 B2 * | 4/2012 | Hoffman | A61B 17/7055 606/280 |
| 8,167,917 B2 * | 5/2012 | Chin | A61B 17/7044 606/280 |
| 8,177,823 B2 * | 5/2012 | Lake | A61B 17/7056 606/276 |
| 8,187,277 B2 * | 5/2012 | Paul | A61B 17/7055 606/280 |
| 8,221,468 B2 * | 7/2012 | Gaines, Jr. | A61B 17/7032 606/264 |
| 8,226,695 B2 * | 7/2012 | Moore | A61B 17/7055 606/286 |
| 8,246,662 B2 * | 8/2012 | Lemoine | A61B 17/7055 606/250 |
| 8,348,981 B2 * | 1/2013 | Cheema | A61B 17/7055 606/286 |
| 8,394,131 B2 * | 3/2013 | Wing | A61B 17/7011 606/264 |
| 8,414,616 B2 * | 4/2013 | Berrevoets | A61B 17/7044 606/250 |
| 8,506,567 B2 * | 8/2013 | Ziemek | A61B 17/8042 606/71 |
| 8,568,459 B2 * | 10/2013 | Uribe | A61B 17/7002 606/264 |
| 8,623,062 B2 * | 1/2014 | Kondrashov | A61B 17/7044 606/246 |
| 8,636,737 B2 * | 1/2014 | Lemoine | A61B 17/7059 606/252 |
| 8,668,721 B2 * | 3/2014 | Miller | A61B 17/7055 606/264 |
| 8,690,923 B2 * | 4/2014 | Lynch | A61B 17/705 606/246 |
| 8,709,049 B2 * | 4/2014 | Klein | A61B 17/7007 606/259 |
| 8,900,276 B2 * | 12/2014 | Purcell | A61B 17/7058 606/280 |
| 8,986,351 B2 * | 3/2015 | Gephart | A61B 17/70 606/246 |
| 9,060,815 B1 * | 6/2015 | Gustine | A61B 17/705 |
| 9,168,068 B2 * | 10/2015 | McClintock | A61B 17/7032 |
| 9,283,004 B2 * | 3/2016 | Hammer | A61B 17/7055 |
| 9,381,044 B2 * | 7/2016 | Robinson | A61B 17/7052 |
| 9,510,866 B2 * | 12/2016 | Hammer | A61B 17/7032 |
| 9,707,015 B2 * | 7/2017 | Hirschl | A61B 17/7056 |
| 9,877,747 B2 * | 1/2018 | Black | A61B 17/7044 |
| 10,265,108 B2 * | 4/2019 | Pischl | A61B 17/8047 |
| 2003/0153913 A1 * | 8/2003 | Altarac | A61B 17/7044 606/278 |
| 2005/0203516 A1 | 9/2005 | Biedermann | |
| 2005/0240181 A1 * | 10/2005 | Boomer | A61B 17/7041 606/914 |
| 2005/0283153 A1 | 12/2005 | Poyner et al. | |
| 2006/0089644 A1 | 4/2006 | Felix | |
| 2006/0129149 A1 | 6/2006 | Iott et al. | |
| 2006/0155284 A1 * | 7/2006 | Doherty | A61B 17/1615 606/86 B |
| 2006/0200133 A1 | 9/2006 | Jackson | |
| 2006/0217710 A1 * | 9/2006 | Abdou | A61B 17/6433 606/54 |
| 2006/0271047 A1 | 11/2006 | Jackson | |
| 2007/0299441 A1 * | 12/2007 | Hoffman | A61B 17/7055 606/250 |
| 2008/0021454 A1 * | 1/2008 | Chao | A61B 17/7044 606/250 |
| 2008/0125781 A1 | 5/2008 | Hoffman et al. | |
| 2008/0177313 A1 | 7/2008 | Lemoine et al. | |
| 2008/0177314 A1 | 7/2008 | Lemoine | |
| 2009/0125067 A1 * | 5/2009 | Mazzuca | A61B 17/7055 606/280 |
| 2009/0312803 A1 | 12/2009 | Austin et al. | |
| 2010/0087867 A1 * | 4/2010 | Klein | A61B 17/7007 606/278 |
| 2013/0184760 A1 * | 7/2013 | Ballard | A61B 17/7041 606/278 |
| 2017/0290608 A1 * | 10/2017 | Neal | A61B 17/7011 |
| 2018/0344361 A1 * | 12/2018 | Fiechter | A61B 17/7055 |
| 2018/0353218 A1 * | 12/2018 | Fiechter | A61B 17/7055 |

* cited by examiner

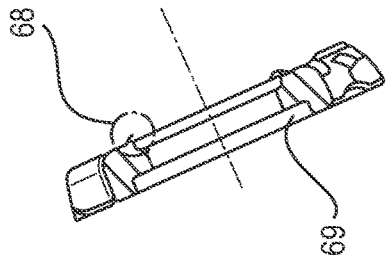
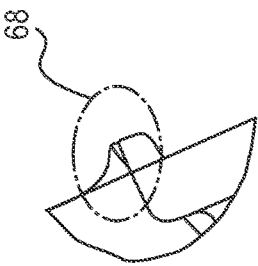
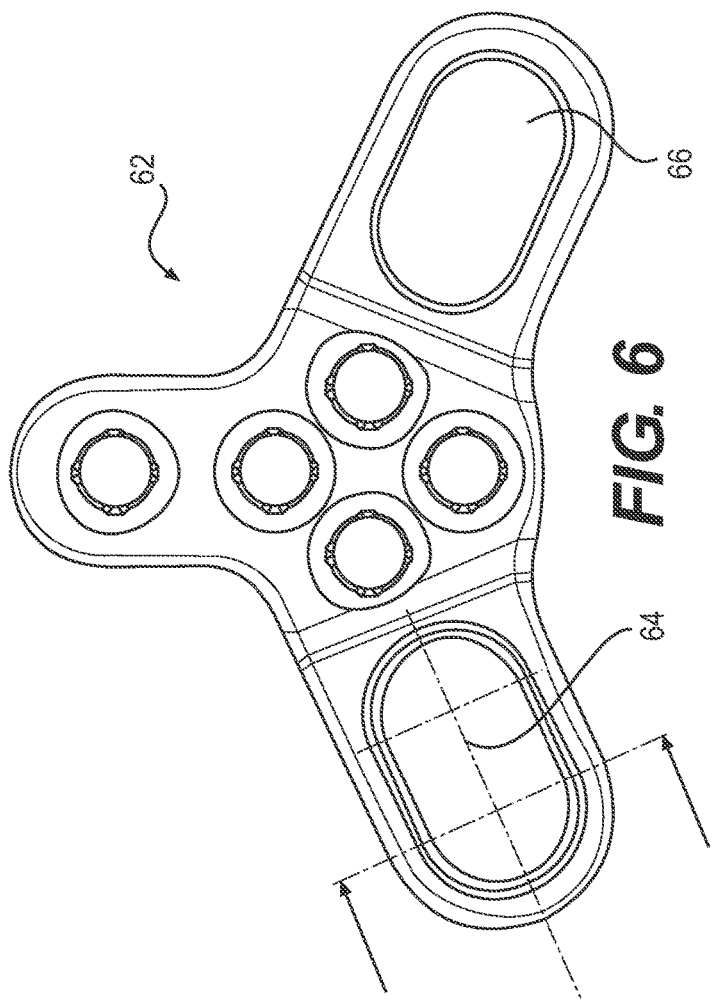

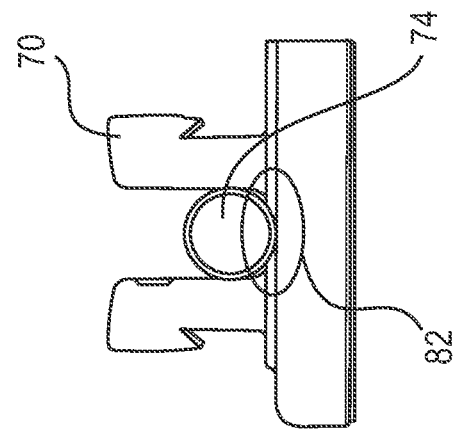
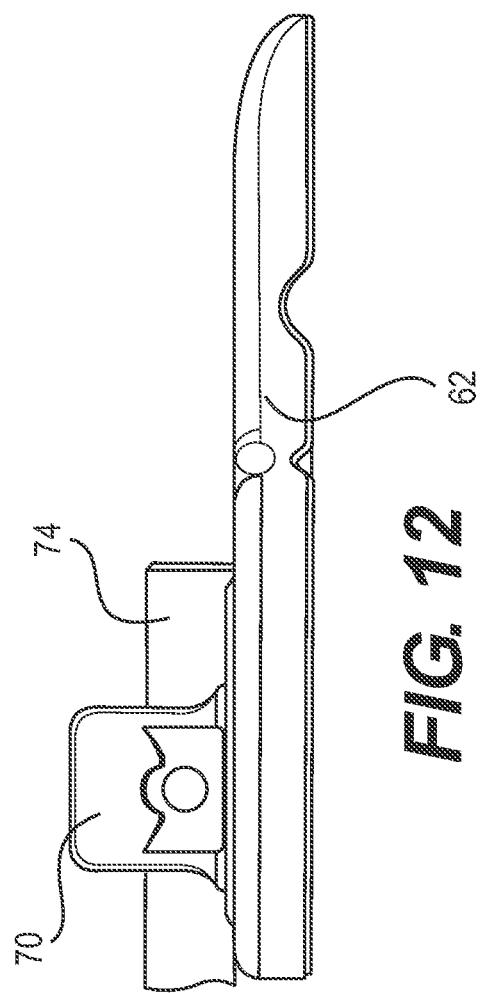
FIG. 13
FIG. 12

SPINE STABILIZATION SYSTEM

CROSS-REFERENCE TO RELATED APPLICATIONS

The present application is a continuation of U.S. application Ser. No. 12/874,845, filed Sep. 2, 2010, which claims priority to U.S. Provisional Application 61/239,309 filed on Sep. 2, 2009. All publications and patent applications mentioned in this specification are herein incorporated by reference to the same extent as if each individual publication or patent application was specifically and individually indicated to be incorporated by reference.

FIELD OF THE INVENTION

The present invention relates to an implant for stabilizing the spine. In particular, the present invention relates to an implant for the cervical spine.

BACKGROUND OF THE INVENTION

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses.

The cervical spine has presented the most challenges for doctors, partially due to the small size of the vertebrae and the spacing between adjacent vertebrae. Even through the spine, because of its proximity to the spinal nerve and the importance the spine plays in day-to-day activities, correcting spinal disorders requires reliable and effective treatments.

Typically, weaknesses in the spine are corrected using devices that fuse one or more vertebrae together. Several artificial materials and implants have been developed to replace the vertebral body, such as, for example, titanium cases, ceramic, ceramic/glass, plastic or PEEK, and carbon fiber spacers. Recently, various expandable prosthetic or expandable cages have been developed and used for vertebral body replacement or in conjunction with other fusion procedures.

During fusion or other corrective procedures, bone plates or other stabilization systems are used to help maintain rigidity of the treated area, maintain compression between adjacent vertebrae, and fix or stabilize the area being fused. Design considerations for fixation systems include ease of use, stability, ability of the surgeon to customize during implantation, and ability of the fixation system to allow for compression. Past fixation system designs have not necessarily alleviated all of the problems. Accordingly, a need exists for a fixation system that can provide a surgeon and patient with stable, customizable fixation systems.

BRIEF DESCRIPTION OF THE DRAWINGS

The invention will be more readily understood with reference to the embodiments thereof illustrated in the attached drawing figures, in which:

FIGS. 6, 7, and 8 illustrates a more detailed view of the slot configured in the occipital plate according to the present invention;

FIGS. 12 and 13 illustrate a side view and front view of the occipital plate and rod receiver according to the present invention.

SUMMARY OF THE INVENTION

The present invention is a spinal stabilization system having an occipital plate configured with a central portion and at least two extension portions extending from the central portion. At least two rod receivers are positioned on each one of the at least two extension portions and the at least two rod receivers are adapted and configured to receive at least two elongated rods. At least two locking assemblies are adapted and configured to retain the at least two elongated rods within the at least two rod receivers. The occipital plate further includes a plurality of holes for receiving bone fasteners and includes a slot for receiving each one of the at least two rod receivers, and the rod receivers being capable of translating and rotating within the slots.

DETAILED DESCRIPTION OF THE INVENTION

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Figure 1:
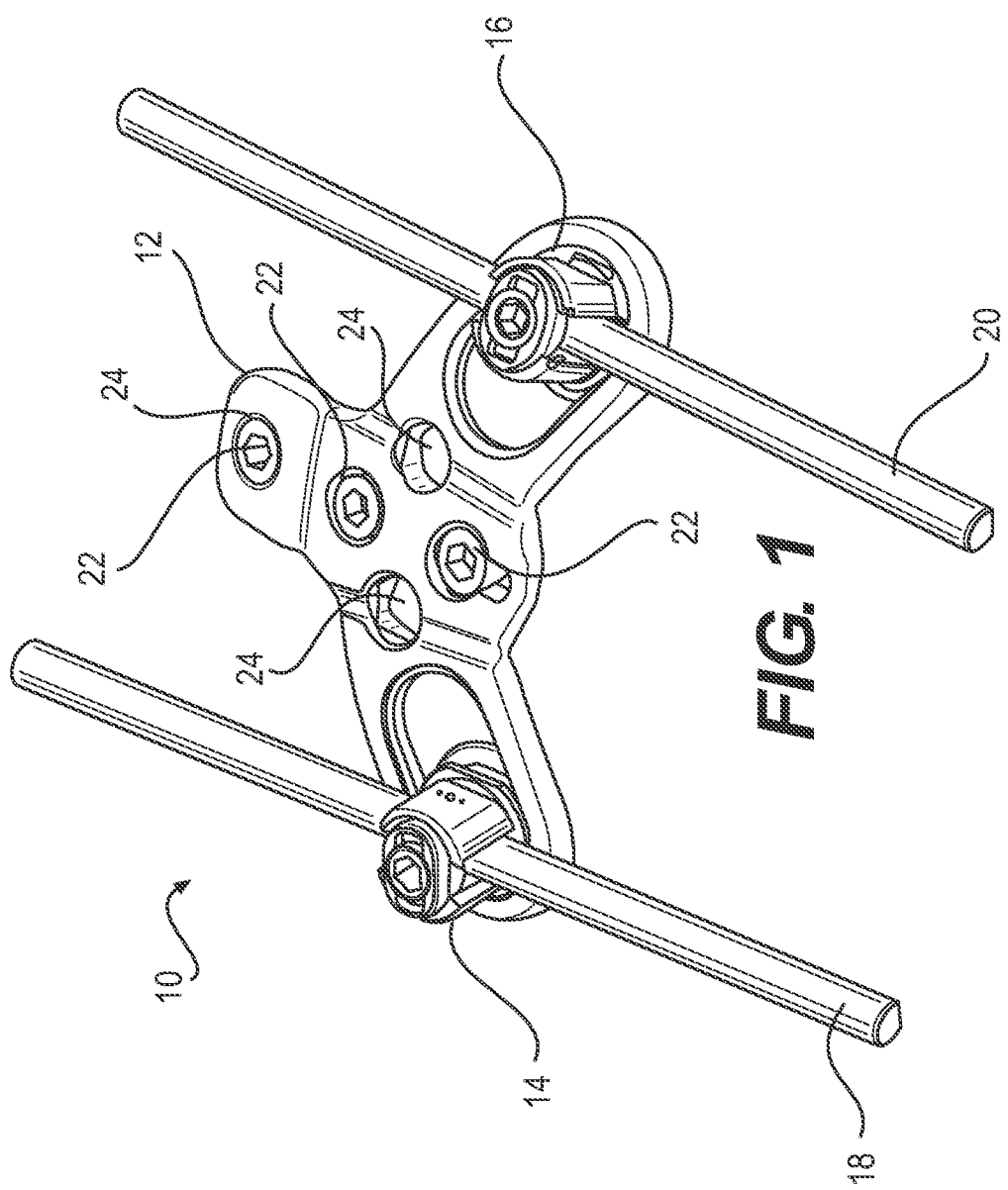
FIG. 1 illustrates an occipital-cervial stabilization system according to one embodiment of the present invention.

FIG. 1 illustrates spinal stabilization systems 10 according to the present invention. System 10 includes at least the following features: an occipital plate 12 having rod receivers 14, 16, and at least 2 elongated rods 18, 20 which are coupled to the rod receivers 14 and 16. The system 10 is attached to the occipital bone through the use of multiple bone fasteners 22 positioned within screw holes 24. The occipital plate 12 and rod receivers 14 and 16 will be discussed in more detail with reference to FIGS. 3-14.

Figure 2:
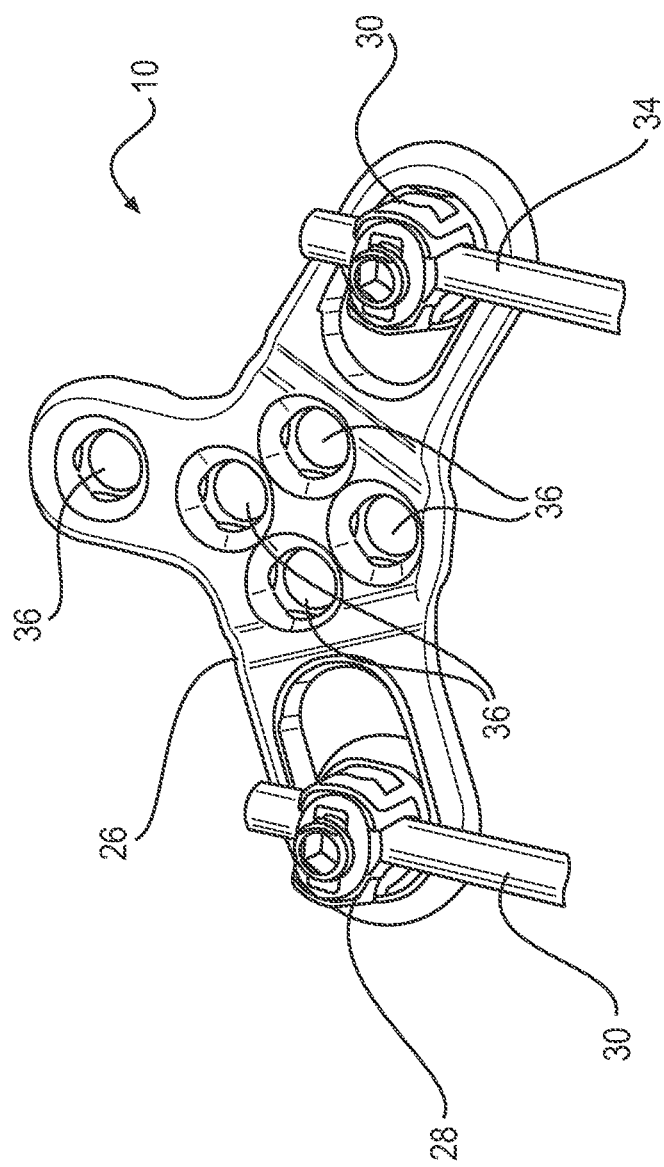
FIG. 2 illustrates another embodiment of an occipital-cervial stabilization system according to the present invention.

FIG. 2 illustrates another embodiment of the spinal stabilization system 11 according to the present invention. This system 11 also provides an occipital plate 26, rod receivers 28, 30, rods 32, 34. The occipital plate 26 is configured with a plurality of screw holes 36 and slots 38.

Figure 3:
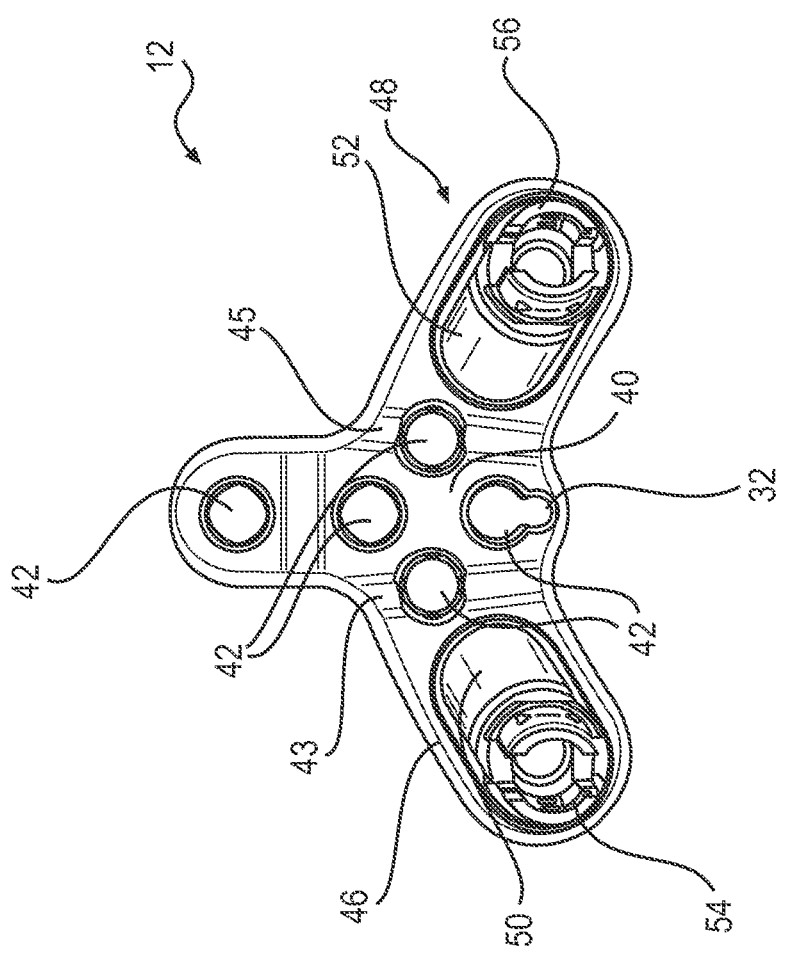
FIG. 3 illustrates a top view of an occipital plate according to the present invention.
Figure 4:
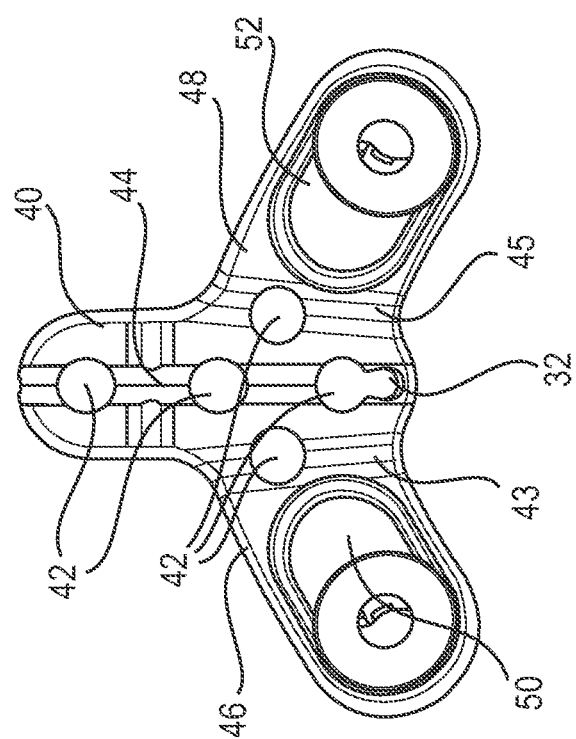
FIG. 4 illustrates a bottom view of the occipital plate illustrated in FIG. 3.

Turning now to FIGS. 3-8, a more detailed description of the occipital plate 12, 26 will be described. Occipital plates 12, 26 may be used in an occipito-cervico-thoracic (OCT) system which is mounted to a patient's occipital bone. The occipital plates 12, 26 may have a compound curvature (FIG. 5) resulting from two unique radii in the axial and in the sagittal planes. The plate 12 comprises a central portion 40 that may be placed on the midline plane or may be slightly offset from the plane of the occipital bone depending on the patient's anatomy and surgeon's preference. The top surface of the central portion 40 contains a plurality of holes 42 for bone fasteners as well as strategically placed grooves 43, 45 to aid in the contouring of the implant. In one embodiment (FIGS. 3 and 4), as illustrated by plate 12, an opening 32 may be provided for allowing cable attachments. The opening 32 is generally connected to the most caudal bone screw hole which allows for cable insertion before or after the plate is mounted onto the occipital bone. It should be noted that although an opening 32 is illustrated in FIGS. 3 and 4, other configurations allowing for cable attachments such as holes, hooks and/or grooves may be used.

FIG. 4 illustrates the bottom surface of occipital plate 12. As illustrated in FIG. 4, central portion 40 also contains the aforementioned holes 42 and grooves 43, 45. In this particular embodiment, a large groove 44 may be provided on the bottom surface of the occipital plate 12. If the plate 12 is positioned directly on the occipital keel, it does not have a good solid contact. In most instances the occipital keep is shaven down to allow for optimal surface contact and no slipping of the plate. In this instance, the occipital keep will serve as the key onto which the occipital plate is positioned. This will allow for increased screw purchase/thread engagement of the bone screw.

Figure 5:
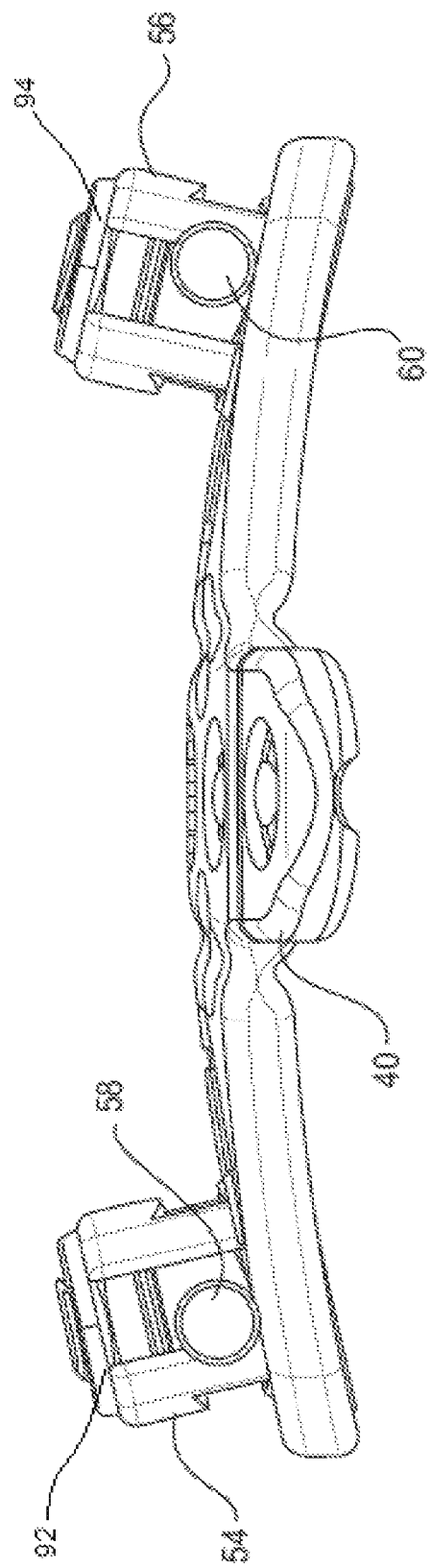
FIG. 5 illustrates a front view of the occipital-cervical stabilization system according to the present invention.

As seen in FIG. 5, the occipital plate 12 comprises the central portion 40, and two curved or straight extension portions 46, 48. Each one of the extension portions 46, 48 includes compound slots 50, 52 that houses a rod receiver 54, 56 that mates with elongated rods 58, 60. The rods 58, 60 are positioned and locked within the rod receiver 54, 56 using a locking cap assembly 92, 94. For ease of rod 58, 60 attachment, each one of the rod receivers 54, 56 translates and rotates within the compound slot 50, 52.

Now turning to FIGS. 6-8, a more detailed description of the compound slot is illustrated with reference to occipital plate 62. The occipital plate 62 is provided with two compound slots 64 and 66. FIGS. 7 and 8 illustrate the cross-sectional view of the compound slot 64. As illustrated in FIGS. 7 and 8, the occipital plate 62 is provided with a mating track 69 geometry that allows free rotation and translation of the rod receivers over the entire range of motion. The occipital plate 62 has a tapered protrusion 68 that borders the flat part of the slots 64, 66 in the occipital plate 62. The protrusion 68 is configured and dimensioned thin enough that it can be permanently deformed when a rod is locked into the rod receivers. The locking set screw in the rod receivers forces the rod down on to the top surface of the plate. This force is strong enough to deform this protrusion, which creates a trough that the rods sit in, which will be discussed in greater detail with reference to FIGS. 12 and 13.

Figure 10:
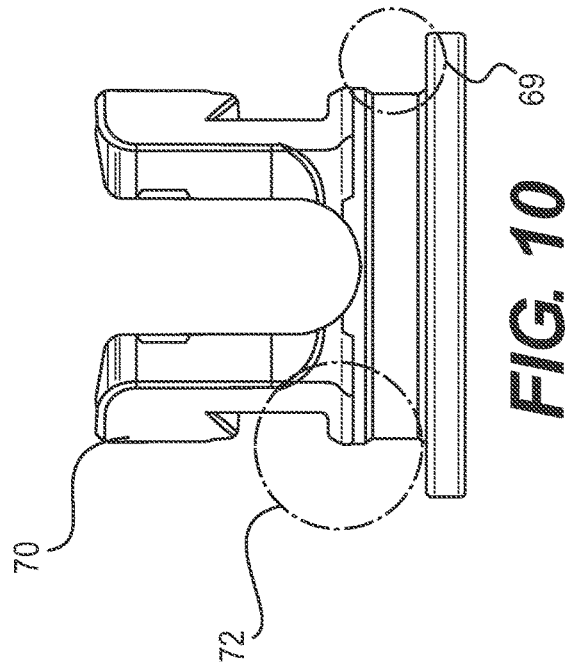
FIGS. 9-11 illustrate a rod receiver according to the present invention.
Figure 11:
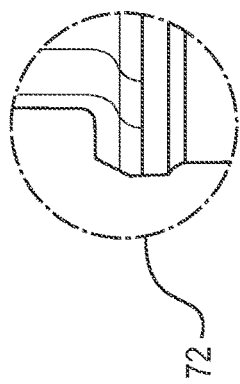
Figure 9:
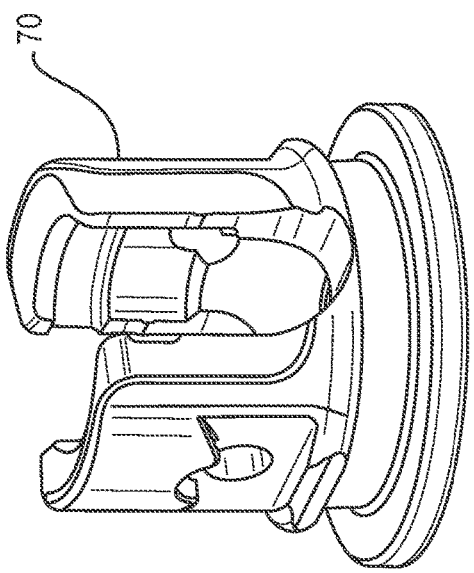

FIGS. 9-11 illustrate a rod receiver 70 in greater detail. Rod receiver 70 is configured to temporarily or permanently assembled to the occipital plate 62. The rod receiver 70 is provided with a taper 72 on both sides of the part, just above the track 69 which allows the rod receiver to rotate and translate within the occipital plate 62. The tapers 72 face the top surface of the rod receiver 70, and are pressed into the occipital plate slots from the bottom surface. Since the rod receiver 70 is pressed into position, the force overcomes the interference that the retainment diameter provides. Once the rod receiver 70 is pressed into place within the occipital plate 62, they cannot be disassembled under normal loading conditions of the occipital plate 62.

Figure 14:
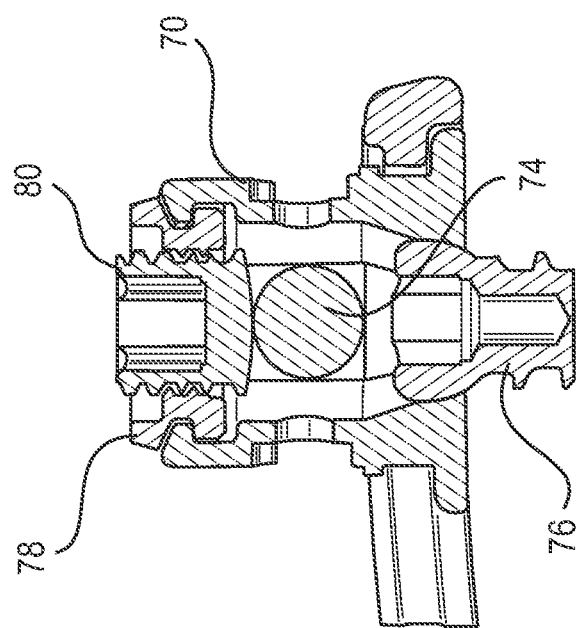
FIG. 14 illustrates a cross-sectional view of the rod receiver and occipital plate according to the present invention.

The rotation of the rod receiver 70 allows for easier positioning of the titanium alloy rod 74, as seen in FIGS. 12 and 13. Each rod receiver 70 contains an opening that may be used to house a bone fastener 76 prior to rod insertion as illustrated in FIG. 14. If a bone fastener 76 is selected to occupy the rod receiver 70, it acts as a far lateral anchoring point for the curved sections protruding from the central section creating a stiffer construct. Each of the rod receivers 70 has a rod capturing feature to aid in the titanium alloy rod reduction, features that aid in the attachment of various instruments for reduction of titanium alloy rods. Once the titanium alloy rod 74 is positioned in the rod receiver 70, locking cap 78 is inserted to prevent the rod 74 from expulsion. A threaded set screw 80 is actuated to lock the construct and prevent the rod 74 from movement.

The implant relies on the clamping force applied to each of the curved sections by the rod 74 and the rod receiver 70. As the set screw 80 actuates inside the locking cap assembly 78, it applies a downward force on the titanium alloy rod 74 and an upward force on the locking cap 78. The rod 74 presses against the top surface of the tapered protrusion of the occipital plate creating a trough 82 that the rod 74 settles into, as illustrated in FIG. 13. This provides full point of contact between the rod 74 and the occipital plate. The axial force on the locking cap 78 is transferred into an upward translation of the rod receiver 70 against the bottom surface within the compound slot.

While the invention herein disclosed has been described by means of specific embodiments and applications thereof, numerous modifications and variations can be made thereto by those skilled in the art without departing from the scope of the invention as set forth in the claims.

What is claimed is:

1. An occipital plate system comprising:
an occipital plate having a central portion and an extension portion extending from the central portion;
a rod receiver positioned on the extension portion, the rod receiver configured to receive an elongated rod; and
a locking assembly configured to retain the rod within the rod receiver,
wherein the extension portion comprises a slot for receiving the rod receiver, and the rod receiver being capable of translating and rotating within the slot,
wherein a tapered protrusion positioned near the slot is configured to be permanently deformed to create a trough when the rod directly contacts the tapered protrusion and is locked on the rod receiver, wherein the tapered protrusion is raised above the slot,
wherein the locking assembly comprises a locking cap and a locking set screw received within the locking cap that forces the rod down deforming the protrusion,
wherein the tapered protrusion borders a circumference of a top surface of the slot of the extension portion.

2. The occipital plate system according to claim 1, wherein the occipital plate further comprises a plurality of holes.

3. The occipital plate system according to claim 2, further comprising a plurality of bone fasteners received in the plurality of holes.

4. The occipital plate system according to claim 2, wherein the occipital plate further comprises a slot positioned adjacent to one of the plurality of holes for receiving a cable.

5. The occipital plate system according to claim 1, wherein the slot is configured with a mating track that allows for free rotation and translation of the rod receiver.

6. The occipital plate system according to claim 1, wherein the tapered protrusion borders a flat portion of each one of the slots.

7. The occipital plate system according to claim 1, wherein the occipital plate further comprises a central groove on a bottom portion of the occipital plate.

8. The occipital plate system according to claim 1, wherein the occipital plate is configured with a compound curvature having two different radii in an axial and sagittal planes.

9. The occipital plate system according to claim 1, wherein the occipital plate is configured with a groove separating the central portion with the extension portion.

10. An occipital plate system comprising:
an occipital plate having a central portion and first and second extension portions extending from the central portion;
a first rod receiver positioned on the first extension portion and a second rod receiver positioned on the second extension portion, the first and second rod receivers each configured to receive an elongated rod; and
first and second locking assemblies configured to retain the elongated rods within the first and second rod receivers, respectively,
wherein the first extension portion comprises a slot for receiving the first rod receiver, and the first rod receiver is capable of translating and rotating within the slot,
wherein a tapered protrusion positioned near the slot is configured to be permanently deformed to create a trough when the rod directly contacts the tapered protrusion and is locked on the rod receiver, wherein the tapered protrusion is raised above the slot,
wherein the first locking assembly comprises a locking cap and a locking set screw received within the locking cap that forces the rod down deforming the protrusion,
wherein the tapered protrusion borders a circumference of a top surface of the slot of the first extension portion.

11. The occipital plate system according to claim 10, wherein the slot is configured with a mating track that allows for free rotation and translation of the first rod receiver.

12. The occipital plate system according to claim 10, wherein the occipital plate further comprises a central groove on a bottom portion of the occipital plate.

13. The occipital plate system according to claim 10, wherein the occipital plate is configured with a compound curvature having two different radii in axial and sagittal planes.

14. An occipital plate system comprising:
an occipital plate having a central portion and at least two extension portions extending from the central portion;
at least two rod receivers positioned on each one of the at least two extension portions, the at least two rod receivers configured to receive at least two elongated rods; and
at least two locking assemblies configured to retain the at least two elongated rods within the at least two rod receivers,
wherein the occipital plate further comprises a plurality of holes for receiving bone fasteners,
wherein each one of the extension portions comprises a slot for receiving each one of the at least two rod receivers, and the rod receivers being capable of translating and rotating within the slots,
wherein a tapered protrusion positioned near at least one of the slots is configured to be permanently deformed to create a trough when one of the rods directly contacts the tapered protrusion and is locked on the rod receiver, wherein the tapered protrusion is raised above the at least one slot,
wherein the at least two locking assemblies comprise a locking cap and a locking set screw received within the locking cap that forces the rod down deforming the protrusion,
wherein the tapered protrusion borders a circumference of a top surface of the slots of each one of the extension portions.

15. The occipital plate system according to claim 14, wherein the slots are configured with a mating track that allows for free rotation and translation of the rod receivers.

16. The occipital plate system according to claim 14, wherein the tapered protrusion borders a flat portion of each one of the slots.

17. The occipital plate system according to claim 14, wherein the occipital plate further comprises a central groove on a bottom portion of the occipital plate.

18. The occipital plate system according to claim 14, wherein the occipital plate is configured with a compound curvature having two different radii in axial and sagittal planes.

19. The occipital plate system according to claim 14, wherein the occipital plate is configured with at least two grooves separating the central portion with the at least two extension portions.

20. The occipital plate system according to claim 14, wherein the occipital plate further comprises a slot positioned adjacent to one of the plurality of holes for receiving a cable.

* * * * *